United States Patent [19]

Alfano et al.

[11] Patent Number: 4,853,595
[45] Date of Patent: Aug. 1, 1989

[54] PHOTOMULTIPLIER TUBE HAVING A TRANSMISSION STRIP LINE PHOTOCATHODE AND SYSTEM FOR USE THEREWITH

[76] Inventors: Robert R. Alfano, 3777 Independence Ave., Bronx, N.Y. 01463; Ardie D. Walser, 1407 Linden Blvd. Apt. 13B, Brooklyn, N.Y. 11212

[21] Appl. No.: 91,123

[22] Filed: Aug. 31, 1987

[51] Int. Cl.$^4$ .................. H01J 43/02; H01J 43/18; H01J 43/28
[52] U.S. Cl. ............................ 313/532; 313/537; 313/542; 250/207; 250/213 VT
[58] Field of Search ............... 313/527, 529, 530, 532, 313/533, 537, 541, 542; 250/213 VT, 207

[56] References Cited

U.S. PATENT DOCUMENTS

| | | | |
|---|---|---|---|
| 3,867,662 | 2/1975 | Endriz | 313/542 |
| 3,914,136 | 10/1975 | Kressel | 313/542 X |
| 4,467,189 | 8/1984 | Tsuchiya | 313/529 X |
| 4,659,921 | 4/1987 | Alfano | 313/528 X |

*Primary Examiner*—Kenneth Wieder
*Attorney, Agent, or Firm*—Irving M. Kriegsman

[57] ABSTRACT

A photomultiplier tube which may be used in time resolving a luminiscence profile emitted from a sample with picosecond resolution using short (picosecond) electrical pulses as a probe and in time resolving an electrical pulse profile produced by fast electronic or optoelectronic devices with femtosecond resolution, using short (femtosecond) laser pulses as the probe is disclosed. The photomultiplier tube includes a photocathode for receiving light and producing emission of electrons in proportion to the intensity of the light, said photocathode having a transmission strip line configuration, accellerating means for accellerating electrons emitted by said photocathode, electron multiplication means for performing electron multiplication on the electrons emitted from the accellerating means, anode means for receiving electrons from the electron multiplication means and producing an analog electrical signal output, means for causing electrons emitted by the photocathode to move through the accellerating means and the electron multiplication means and then impinge on the anode means, and means connected to said photocathode for receiving an ultrafast voltage signal.

18 Claims, 5 Drawing Sheets

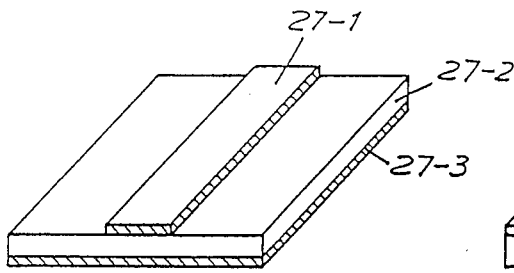
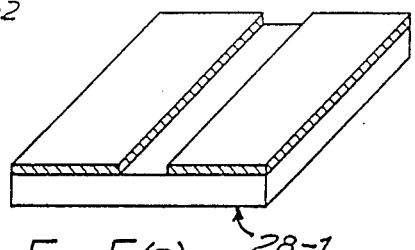
FIG.5(A)　　　　FIG.5(B)
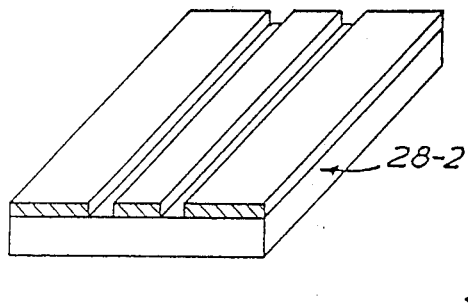
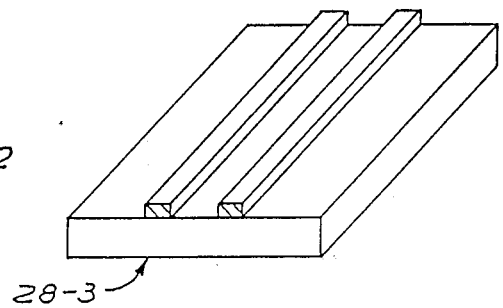
FIG.5(C)　　　　FIG.5(D)

$$V_{OUT}(\tau) = \int L(t) v(t+\tau) dt$$

PHOTOMULTIPLIER TUBE HAVING A TRANSMISSION STRIP LINE PHOTOCATHODE AND SYSTEM FOR USE THEREWITH

BACKGROUND OF THE INVENTION

The present invention relates generally to photomultiplier tubes and more particularly to a photomultiplier tube constructed for use in time resolving picosecond luminescent events and/or picosecond voltage pulse.

A photomultiplier tube is a well known type of photosensitive device that is commonly used in time resolving optical signals.

Basically, a photomultiplier tube comprises a photocathode, an electron multiplier and an anode, all disposed in an evacuated glass housing, with potential differences set up between the electrodes and the electron multiplier to cause photoelectrons emitted by the photocathode to pass through the electron multiplier and or to the anode.

When light strikes the photocathode, photoelectons are emitted into the vacuum in proportion to the intensity of the light. These photoelectrons are multiplied by the electron multiplier and then collected by the anode as an output signal.

Because of the electron multiplication, photomultiplier tubes are uniquely sensitive among photosensitive devices currently used to detect radiant energy in the ultraviolet, visible, and near infrared regions. Photomultiplier tubes also feature relatively fast time response and low noise.

The photocathode in a photomultiplier tube is generally arranged in either a side-on or a head-on configuration. In the side-on type configuration the photocathode receives incident light through the side of the glass housing, while, in the head-on type, light is received through the end of the glass housing. In general, the side-on type photomultiplier tube is widely used for spectrophotometers and general photometric systems. Most of the side-on types employ an opaque photocathode (reflection-mode photocathode) and a circular-cage structure electron multiplier which has good sensitivity and high amplification at relatively low supply voltage.

The head-on type photomultiplier tube has a semitransparent photocathode (transmission-mode photocathode) deposited upon the inner surface of the entrance window while in the side-on type the photocathode is a separate structure. Because the head-on type provides better uniformity and lower noise, it is frequently used in scintillation detection and photon counting applications.

The electron multiplier in a photomultiplier tube is usually either a series of electrodes, called dynodes, or a microchannel plate. As is known, a microchannel plate (MCP) is a form of secondary electron multiplier consisting of an array of millions of glass capillaries (channels) having an internal diameter ranging from 10 $\mu$m to 20 $\mu$m fused into the form of a thin disk less than 1 mm thick. The inside wall of each channel is coated with a secondary electron emissive material having a proper resistance and both ends of the channel are covered with a metal thin film which acts as electrodes, thus each channel becomes an independent secondary electron multiplier.

When a voltage is applied between the both sides of an MCP, an electric field is generated in the direction of the channel axis. When an electron hits the entrance wall of the channel, secondary electrons are produced. These secondary electrons are accelerated by the electric field, and travel along the parabolic trajectories determined by their initial velocity. Then they strike the opposite wall and produce other secondary electrons. This process is repeated many times along the channel, and, as a result, the electron current increases exponentially towards the output end of the channel.

The photocathode in a head-on type photomultiplier tube is generally circularly shaped and in a side-on photomultiplier tube is usually in the shape of a portion of a cylinder.

In U.S. Pat. No. 3,885,178 there is disclosed a photomultiplier tube (PMT) which converts a received light signal to an output electrical signal of substantially greater intensity by employing a photocathode to convert incident light to free electrons, a plural dynode accelerating structure for effectively multiplying the free electrons, and an impact ionization diode (IID) for further multiplying and collecting the free electrons to provide a corresponding electrical output signal. The PMT can be an electrostatic device, in which the photocathode and the dynodes are mounted in opposed staggered positions, or a static crossed field device, in which the photocathode and the dynodes all are mounted opposite an accelerating rail and a magnetic field is provided to urge the electrons laterally along the tube. The IID's junction is reverse biased and the entire didode is maintained at a substantially higher potential than the last dynode. The PMT can be gain controlled or turned off without affecting dynode potentials by controlling the IID's potential. Due to the gain provided by the IID, dynode current can be reduced greatly, thereby to increase substantially the tube's life without affecting it's overall gain.

One of the limitations of photomultiplier tubes is that although they have a relatively fast time response they are not capable of time resolving events in the picosecond time regime. On the other hand, a device that does have the capability of time resolving events in the picosecond time regime is the streak camera.

Streak cameras are about fifteen years old in the art and have been used, hitherto, to directly measure the time dynamics of luminous events, that is to time resolve a light signal. A typical streak camera includes an entrance slit which is usually rectangular, a streak camera tube, input relay optics for imaging the entrance slit onto the streak camera tube, appropriate sweep generating electronics and output-relay optics for imaging the streak image formed at the output end of the streak camera tube onto an external focal plane. The image at the external local plane is then either photographed by a conventional still camera or a television camera. The streak camera tube generally includes a photocathode screen, an accelerating mesh, sweeping electrodes and an phosphor screen. The streak camera tube may also include a microchannel plate. Light incident on the entrance of the streak camera is converted into a streak image which is formed on the phosphor screen with the intensity of the streak image from the start of the streak to the end of the streak corresponding to the intensity of the light incident thereon during the time window of the streak. The time during which the electrons are swept to form the streak image is controlled by a sweep generator which supplies a very fast sweep signal to the sweeping electrodes. The input optics of the streak camera, in the past, has been a single lens.

In U.S. Pat. No. 4,659,921 a light detector which can be gated on and off over an ultrashort time window, such as in picoseconds or femtoseconds, is disclosed. The light detector includes, in one embodiment, an input slit for receiving a light signal, relay optics, a sweep generator and a tubular housing, the tubular housing having therein a photocathode, an accelerating mesh, a pair of sweeping electrodes, a microchannel plate, a variable aperture and a dynode chain. Light received at the inputslit is imaged by the relay optics onto the photocathode. Electrons emitted by the photocathode are conducted by the accelerating mesh to the sweeping electrodes where they are swept transversely across the tubular housing at a rate defined by the sweep generator over an angular distance defined by the sweeping electrodes, in a similar manner as in a streak camera. Swept electrons strike the microchanel plate where electron multiplication is accomplished. Exiting electrons which pass through the variable aperture and which strike the first dynode (cathode) in the dynode chain are further multipled and outputted from the last dynode anode in the dynode chain as an analog electrical signal, the analog electrical signal corresponding to the intensity of the light signal during the time window over which swept electrons are picked up by the first dynode. In another embodiment of the invention all of the dynodes in the chain except for the last dynode are replaced by a second microchannel plate.

In U.S. Pat. No. 4,467,189 a framing tube is disclosed which includes a cylindrical airtight vacuum tube, a shutter plate, and a ramp generator. The container has a photocathode at one end thereof and a fluorescent screen at the other end thereof which is opposite to the photocathode. The shutter plate is disposed between and parallel to the surface of the photocathode and fluorescent screen and has a multiplicity of through holes perforated perpendicular to its surface. The shutter plate also carries at least three electrodes that are disposed perpendicular to the axis of the through holes and spaced parallel to each other. The electrodes divide the surface of the shutter plate into a plurality of sections. The ramp generator is connected to the electrodes. The ramp voltage generated changes in such a manner as to reverse its polarity, producing a time lag between the individual electrode. Developing an electric field across the axis of the through holes in the shutter screen, the ramp volage controls the passage of the electron beams from the photocathode through the through holes. A framing camera includes the above-described framing tube and an optical system. The optical system includes a semitransparent mirror that breaks up the light from the object under observation into a plurality of light components and a focussing lens disposed in the path through which each of the light components travels. Each of the light components correspond to each of the sections on the shutter plate. The images of a rapidly changing object are produced, at extremely short time intervals, on different parts of the fluorescent screen.

It is an object of this invention to provide a new and improved photomultiplier tube.

It is another object of this invention to provide a photomultiplier tube that can be used in time resolving picosecond luminescent events and/or picosecond voltage pulses.

It is still another object of this invention to provide a new type of photocathode for a photomultiplier tube.

SUMMARY OF THE INVENTION

A photomultiplier tube which can be used to time resolve voltage pulses or light pulses with femtosecond and picosecond resolution, respectively, constructed according to this invention comprises a housing having therein a photocathode for receiving light and producing emission of electrons in proportion to the intensity of the light impinging thereon, the said photocathode having a transmission strip line configuration, electron multiplication means for performing electron multiplication on the emitted electrons, anode means for receiving electrons from the electron multiplication means and producing an analog electrical signal output, means for causing electrons emitted by the photocathode to move through the electron multiplication means and then impinge on the anode means, and means connected to said photocathode for receiving an ultrafast voltage signal.

The photomultiplier may be used in time resolving a luminescence profile emitted from a sample with picosecond resolution using short (picosecond) electrical pulses as a probe and in time resolving an electrical pulse profile produced by fast electronic or optoelectronic devices with femtosecond resolution, using short (femtosecond) laser pulses as the probe.

Various features and objects will appear from the description to follow. In the description, reference is made to the accompanying drawing which forms a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts:

FIG. 5(a) is a perspective view of an embodiment of the photocathode shown in FIG. 3;

FIGS. 5B, 5C and 5D are perspective views of photocathode configurations for the photomultiplier tube shown in FIG. 3;

DETAILED DESCRIPTION OF PREFERRED EMBODIMENTS

The present invention is directed to a new and novel photomultiplier tube and to a method and system of using the new and novel photomultiplier tube for time resolving picosecond luminescence events and/or picosecond voltage pulses. The system incorporates high speed switches (such as picosecond photoconductive switches or pulse generators) with the gain and sensitivity of the specially designed photomultiplier. The resolution of the system constructed using the photomultiplier tube of this invention is dictated by the convolution of a biasing picosecond voltage pulse that is applied to the photocathode in the photomultiplier tube with an incident picosecond/femtosecond light pulse that is also applied to the photocathode in the photomultiplier tube. Since the photoelectric phenomenon in instantaneous the time response of this system is $-130$ fs for a 20 $\mu$m beam size. The photomultiplier features an area photocathode which is in the form of transmission strip line. The system can be used to (1) measure picosecond voltage pulse or (2) measure the luminescence profile of a sample with femtosecond resolution.

Figure 1:
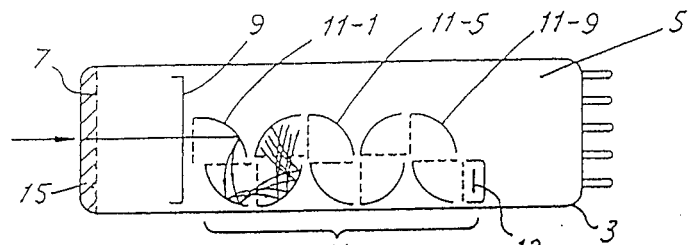
FIG. 1 is a simplified diagram of a conventional head-on type photomultiplier tube.
Figure 2:
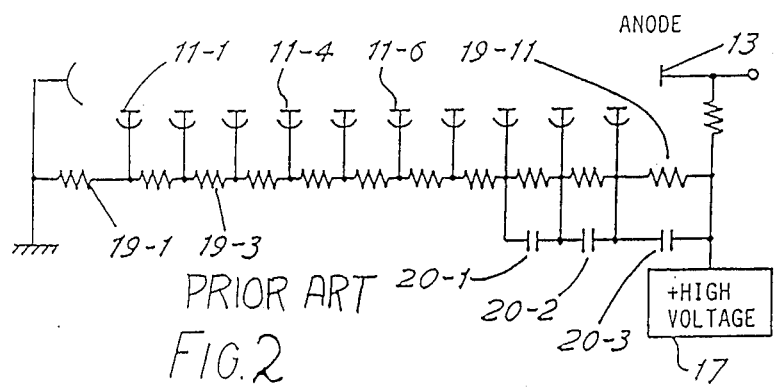
FIG. 2 is a schematic diagram illustrating the voltage-divider network in the photomultiplier tube shown in FIG. 1.

Referring now to the drawings, there is shown in FIG. 1 a simplified cross-section view of one type of prior art photomultiplier tube, the tube being identified by reference numeral 3. Tube 3 includes an evacuated tubular housing 5 having on the outside a set of pins 6 and on the inside a photocathode 7, an accelerating mesh 9 an electron multiplier 11 in the form of a chain of dynodes 11-1 through 11-10 and an anode 13. Photocathode 7 is in the form of a coating deposited on the inner surface of an entrance window 15 at the head of housing 5. For convenience, the circuitry for applying successively increased voltages to the electrodes and the accellerating mesh are not shown in FIG. 1 but instead are shown separately in FIG. 2. As can be seen in FIG. 2, the circuitry comprises a high voltage source 17, and a plurality of series-connected resistors 19-1 through 19-12 and a plurality of capacitors 20-1 through 20-3.

Figure 3:
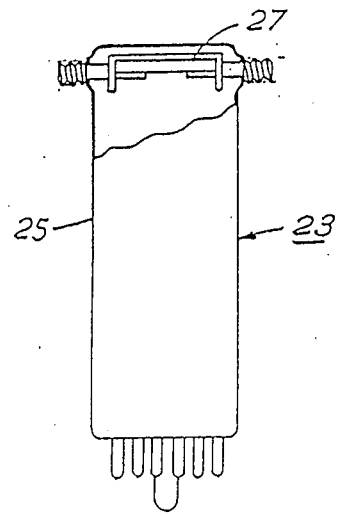
FIG. 3 is a front elevation view partly broken away in section of one embodiment of a photomultiplier tube constructed according to the teachings of the present invention.
Figure 4:
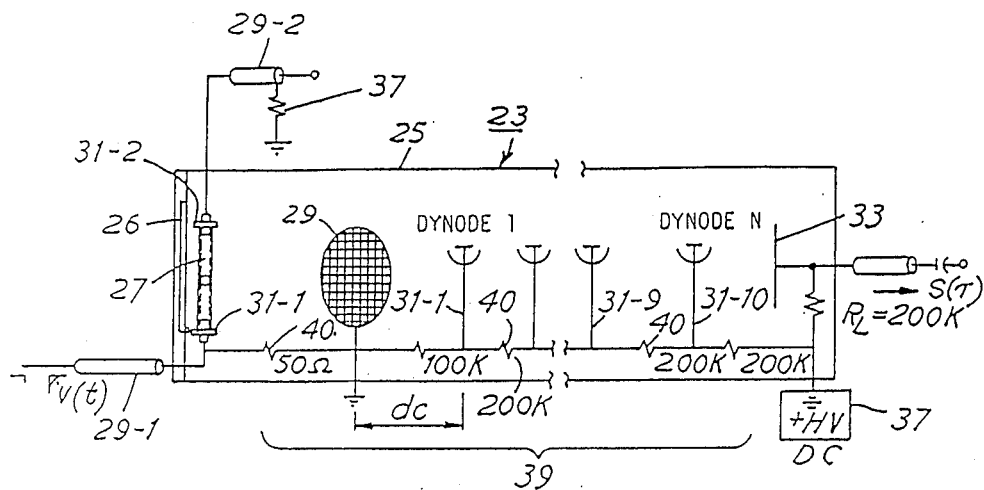
FIG. 4 is a schematic diagram of the photomultiplier tube shown in FIG. 3 and the associated circuitry.

Referring now to FIG. 3, there is shown a front elevation view of a photomultiplier tube constructed according to the teachings of this invention and identified by reference numeral 23. A schematic of photomultiplier 23 and the associated circuitry is shown in FIG. 4.

Tube 23 comprises a tubular glass housing 25. Disposed inside of housing 25 are a variable aperture 26, a photocathode 27, an accelerating mesh 29 for accelerating electrons emitted by photocathode 27, a dynode chain 31, the dynode chain 31 comprising a plurality of dynodes 31-1 through 31-10, and an anode 33. Disposed outside of housing 25 are a set of pins 35.

Housing 25, mesh 29 and dynode chain 31 are of the same construction as in a conventional photomultiplier tube. However, because the temporal width of the electrical pulses to be analyzed are in the picosecond regime, it is necessary to modify the photocathode of the photomultiplier 23 so as to have a transmission line configuration so that it can faithfully carry pulses of this duration. Accordingly, photocathde 27 is constructed in a transmission line configuration. In the embodiment shown the particular transmission line configuration employed is a microstrip line (see FIG. 5A) and includes a strip shaped upper conductor 27-1 made of a suitable photoconductive material, a substrate 27-2 of dielectric material underneath conductor 27-1 made of a suitable material such as glass and a lower conductor 27-3 below substrate 27-2, made of a suitable conductive material such as copper or gold. The type of material choosen for the upper conductor 27-1 is a determining factor in what frequency range the photomultiplier will respond to the light radiation. Examples of some but not all of the photcathode materials that may be used for the upper conductor 27-1 and the frequency range to which they will respond are as follows: Sb-Cs, ultraviolet to visible; AG-O-Cs, visible to 1000 nm; Sb-K-Cs, ultraviolet to visible and Na-K-Sb-Cs, ultraviolet to near infrared. Microstrip 27 is designed for a 50 characteristic impedance Zo such that standard 50 ohm cables 29 connected to subminiature coaxial to strip line microwave launchers 31 can be used. Photomultiplier 23 operates in the transmission-mode, hence, all materials of the photocathode microstrip 27 are transparent or translucent.

Other transmission line configurations that may be employed include the slotline 28-1 (FIG. 5B) the coplanar waveguide 28-2 (FIG. 5(C) and coplanar strips 28-3 (FIG. 5D).

As can be seen in FIG. 4, photocathode 27 is mounted between the two subminiature coaxial to strip line microwave launchers 31-1 and 31-2. In use, an optical beam 35 (probing or luminescence) is focused by a lens 36 on the strip line 27 the size of the spot depending on the size of aperture 26. An electrical pulse V(t) propagates through a coaxial cable 29-1 (Zo=50) across the photocathode microstrip 27 and is then terminated with a 50 ohm resistor 37 to reduce reflection of the voltage pulse. The 50 ohm terminator may be replaced with a 50 ohm coaxial cable. This will allow constant monitoring of the electrical pulse V (t), or its use in triggering other devices. The voltage pulses V(t) negatively bias the photocathode-microstrip 27 with respect to accellerating mesh 29 which is grounded. Thus, when the optical and electrical pulses overlap in the strip line 27, the emitted electrons will travel towards the accellerating mesh 29. The distance between the mesh 29 and the photocathode microstrip 27 is such that the electric field between them is strong enough to accelerate all the emitted electrons with the same initial, velocity, thus keeping them well bunched. The distance dc should be selected such that electrons will travel towards the grid only when the photocathode-microstrip is biased by the voltage pulses V(e) (probing and unknown). A positive dc voltage 37 is placed between the mesh 29 and anode 33. This voltage is divided between dynode stages by a voltage divider network 39 in the form of a plurality of resistors 40, through the load resistance RL should be made small as possible, such as for example 200K for optimum output linearly and frequency response.

The size of the adjustable aperture 26 will determine the resolution of the system. For example, aperture diameters of 20 m, 10 $\mu$m, 5 $\mu$m, 100 $\mu$m and 200 $\mu$m will produce resolutions of 130 femtoseconds, 65 femtoseconds, 32 femtoseconds, 6.5 femotoseconds, 0.65 picoseconds and 1.3 picoseconds, respectively.

Figure 6:
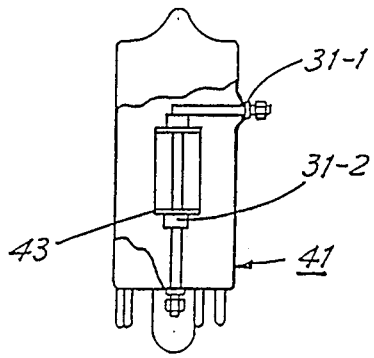
FIG. 6 is a front elevational view partly in section of another embodiment of a photomultiplier tube constructed according to the teachings of the present invention.

Another embodiment of a photomultiplier tube constructed according to this invention and identified by reference numeral 41 is shown in FIG. 6. In photomultiplier 41, the photocathode 43 is in the form of a microstrip as in the FIG. 3 embodiment but is disposed for illumination from the side rather than from the top.

Figure 7:
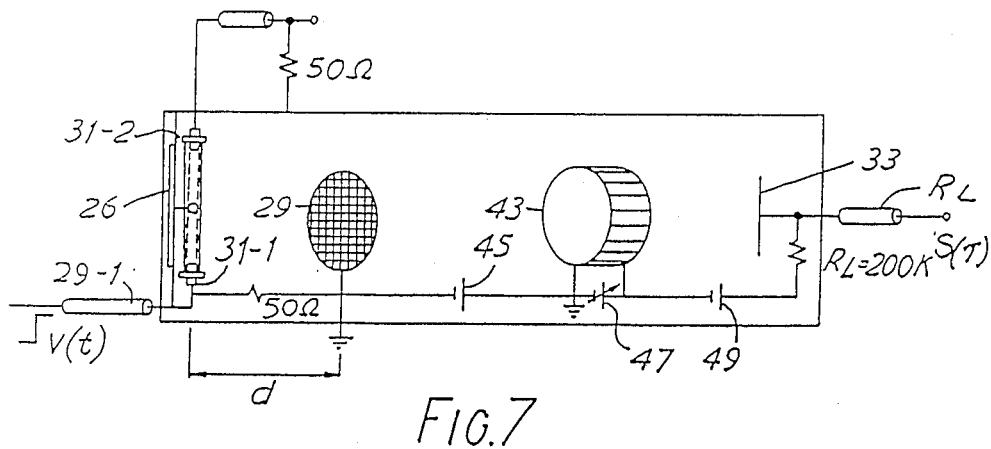
FIG. 7 is a schematic diagram of another version of a photomultiplier tube constructed accoding to this invention.

In FIG. 7 there is shown a schematic of another embodiment 51 of a photomultiplier according to this invention. In FIG. 7, the dynodes and voltage divider are replaced with a microchannel plate 43. Three dc voltage sources 45, 47 and 49 are used to guide the emitted electrons through the microchannel plate 43 onto the anode.

Figure 8:
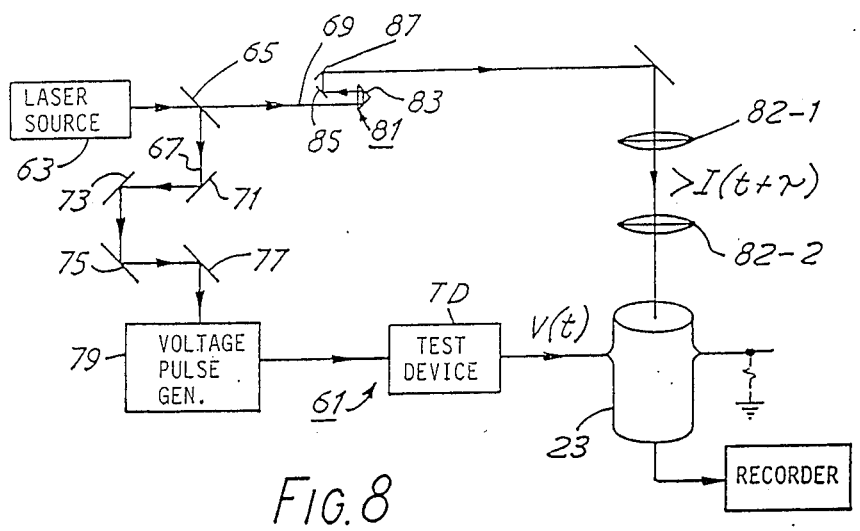
FIG. 8 is a diagram of a system for time resolving a voltage pulse using the photomultiplier of the present invention.

Referring now to FIG. 8 there is shown a system 61 constructed according to this invention and using photomultiplier 23 for measuring a picosecond voltage profile V(t).

The system 61 includes a laser light source 63 for generating optical pulses from 30 ps to 120 fs at 10 Hz to 100 Mhz. A pulse of light from source 63 impinges on a beamsplitting mirror 65 where it is split into a reflected pulse 67 and a transmitted pulse 69.

The reflected pulse I(t) having a pulse width $\Delta$to is reflected off a set of four mirrors 71, 73, 75 and 77, which are used to increase the path length of the reflected pulse, and impinges on a pulse generator 79 (ie. a photoconductive switch). The voltage pulse produced by pulse generator 79 is used to excite a test device TD. Test device TD produces an unknown signal pulse V(t) with a pulse Width of $\Delta$tv At time t the voltage pulse V(t) biases the photocathode 27 microstrip in photomultiplier 23 as it propagates across.

Figure 9:
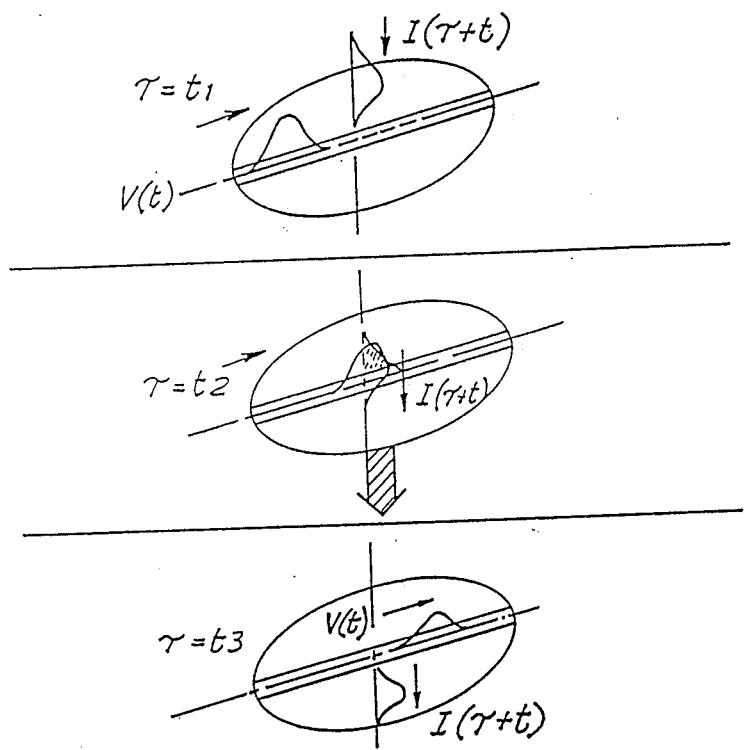
FIGS. 9(a) through 9(c) are schematic representations of the propagation on the voltage and optical pulses in the system in FIG. 8 as they overlap in the photocathode in the photomultiplier tube.

A transmitted or probe pulse $I(t+\tau)$ 69 having a pulse width $\Delta$to is passed through an optical delay line 81 collimated by first lens 82-1 and brought to focus by a second lens 82-2 upon the photocathode microstrip in photomultiplier tube 23 at time $t+\tau$. Delay line 81 is made up of a movable prism 83 and a pair of mirrors 85 and 87. As can be appreciated, electrons will emit and propagate to the first dynode of photomultiplier 23 only when the unknown voltage pulse V(t) and the optical probe pulse $I(t+\tau)$ 69 overlap in time and space in the photocathode-microstrip 27. FIGS. 9(a) through 9(c) give a schematic representation of this process. The number of electrons emitted from the photocathode-microstrip 27 is proportional to the amount of overlap of the unknown voltage pulse V(t) 67 and the probing optical pulse $I(t+\tau)$ 69. The amount of overlap of the two pulses is controlled by the amount of time delay between them.

The time delay between the unknown voltage pulse V(t) 67 and the optical probe pulse $I(t+\tau)$ 69, is varied by varying the optical distance that the optical probe pulse 69 travels with respect to the optical distance traveled by the activating optical pulse of the pulse generator.

The signal produced at delay time $\tau$:S($\tau$) from the unknown voltage pulse V(t) and the delayed optical probe pulse $I(t+\tau)$ arising from the electrons emitted from the photocathode-microstrip 27 is given by the formula $$S(\tau) = \int_{-\infty}^{\infty} KV(t)I(t + \tau)dt$$

where S( ) is the signal from electrons emitted from the photocathode-microstrip 27 at $\tau$, K is the response of the photoelectric material on microstrip 27, V(t) is the unknown voltage pulse and $I(t+\tau)$ is the probing optical pulse. Since the response of the photoelectrical phenomena is instantaneous ($10^{-14}$ s) the variable K is assumed constant and may be removed from inside the integral. Hence, $$S(\tau) = K \int_{-\infty}^{\infty} V(t)I(t + \tau)dt$$

The emitted photoelectrons are accelerated by the electric field produced by V(t) striking the first dynode and producing secondary emissions. These secondary electrons then impinge upon the next dynodes to produce additional secondary electron emissions etc. Repeating this process over successive dynode stages, a high current amplification is achieved. This process is slow. The time response comes from overlap of V(t) and I(t).

As is known, photomultiplier tubes or multichannel plates tubes have gains on the order of $10^2$ to $10^7$. The output signal of the photomultiplier tube is highly susceptible to fluctuations in the power supply voltage, hence the power supply tube is dynodes 2 to n should be very stable and exhibit minimum ripple, drift and temperature variation.

The current collected by the anodes is proportion to S( ):

$$S(\tau) = GK \int_{-\infty}^{\infty} V(t)I(t + \tau)dt$$

is sent through a load resistor R giving the following output voltage signal:

$$V_0(\tau) = R1S(\tau) = R1GK \int_{-\infty}^{\infty} V(t)I(t + \tau)dt = \int_{-\infty}^{\infty} V(t)I(t + \tau)dt$$

at $\tau$, the Vo($\tau$) is used to drive the vertical axis of the display. Hence, the output signal Vo($\tau$) at $\tau$ is proportional to the unknown voltage pulse V(t) at $\tau$ times the gain of the modified photomultiplier.

If the width of the optical probe pulse $\Delta$to is less than the width of the unknown voltage pulse $\Delta$t$_v$, i.e. $\Delta$to<<$\Delta$tv then the unknown voltage pulse can be time resolved in the femtosecond regime for this is the limit of the optical pulse width delta t0. It should be noted that the time resolution of this technique does not depend upon the response time of the photomultiplier 23 or the transit time ($T_t$) of the growing electron packet (current), but on the width of the probing optical pulse $\Delta$to.

The resolution of photomultiplier 23 is determined by the convolution time of the optical pulse ($\tau$o) and the traveling electrical signal as they co propogate through the photocathode material. Since the two signals travel orthogonal paths, the temporal resolution t is the time it takes for the probe pulse to transverse through photocathode material convolved with the transit time of the electrical signal across the optical beam waist.

For a beam spot size of 20 μm and a transmission strip line photocathode with a glass substrate (n=1.5·ϵre=3.77) and a 50Ω characteristic impedance Z0, the temporal resolution is 130 fs. The 20 μm beam waist is obtained by placing an aperture over the photocathode, which also helps to reduce unwanted scattered light.

The electron transit time is the determining factor in the rate at which the output data can be obtained. To receive continuous data using a 100 MHz CW laser, the electron transit time $T_t$ must be less than the repetition rate of the laser (i.e. $T_t <$ ions). Using a pulse laser at a 10 Hz repetition rate places a lower constraint on the transit time $(T_t)$ of the modified photomultiplier. Todays photomultipliers have electrons transit times $(T_t)$ of 7.8–135 ns. Hence, depending on whether its a CW or a pulse setup the appropriate modified photomultiplier can be produced. Another limiting factor in the acquisition rate of data is the repetition rate of the voltage pulse generator. Using optoelectronic switches, repetition rates can be acquired in the GHz (~250 GHz). Hence, there is no problem in using this technique in the CW or pulse mode of operation.

Figure 10:
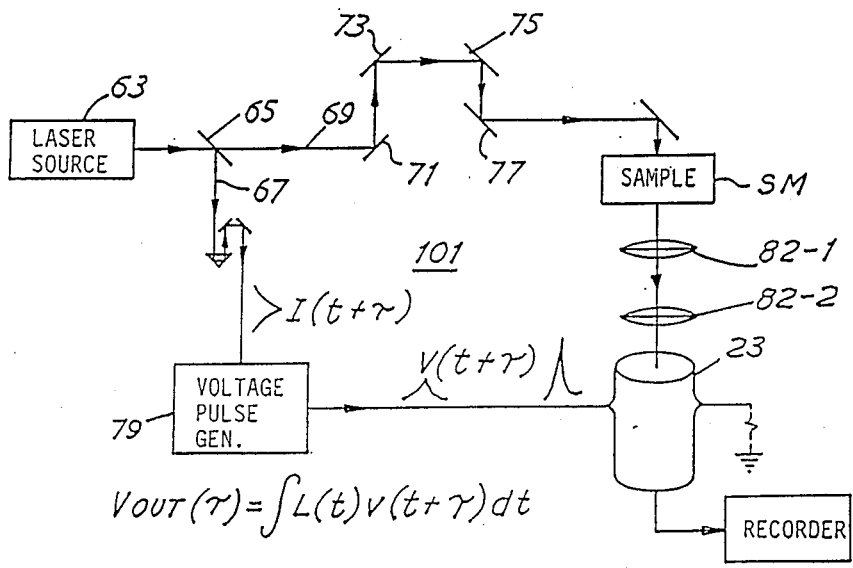
FIG. 10 is a diagram of a system for time resolving luminescence of a sample using the photomultiplier of the present invention.

Referring now to FIG. 10 there is shown a system 101 for the measurement of luminescence profiles or laser pulse shapes in time, better than with picosecond resolution. In FIG. 10, the optical pulse $I(t+\tau)$ (i.e. the reflected portion of the beam from beam splitter 65) with pulse width $\Delta t_o$, strike pulse generator 79. The output signal of pulse generator 79, is voltage pulse $V(t+\tau)$ with a pulse width t. This voltage pulse biases the photocathode-microstrip in photomultiplier 23 as it propagates across the strip line at time $t+\tau$.

The optical pulse $I(t)$ (i.e. the transmitted portion from beamsplitter 65) with pulse width $\Delta t_o$ is used to excite a sample material sm (i.e. semiconductor, liquids, polymers etc.). The sample produces a luminescence profile L(t) with pulse polymers etc.). The sample produces a luminescence profile L(t) with pulse width $\Delta t_L$ that is incident upon the photocathode-microstrip at time t. Once again, the electrons will emit and propagate to the 1st dynode of the modified photomultiplier, only when the voltage pulse $V(t+\tau)$ and luminescence pulse L(t) overlap in time and space in the photocathode-microstrip. From this point on, this system is identical to the system used to measure the unknown voltage described above. Except, in this case the voltage pulse width $\Delta t_v$ is less than the pulse width $\Delta t_L$ of the luminescence (i.e. $\Delta t_v << \Delta t_L$). Hence, the output single $V_o(\tau)$ at delay time that is used to drive the horizontal axis of the display is as follows:

$$V_o(\tau) = K \int_{-\infty}^{\infty} L(t)V(t + \tau)dt$$

K=gain of photomultiplier

The resolution in this case is dictated by the width of the probing voltage pulse $\Delta t_v$. Using an optoelectronic switch as the pulse generator, voltage pulses with pulse widths t in the picosecond regime can be generated. Hence, the luminescence profile of the sample material can be measured with picosecond resolution. Shorter voltage pulse may be possible in the future which will allow measurements of luminescence decay in femtosecond regime.

Note, the output signal for each system, is proportional to the cross correlation of the optical pulse I(t) and the voltage pulse V(t) at delay $\tau$. The time resolution of both techniques do not depend upon the response time of the modified photomultiplier or electron transmit time, but on the width of the narrowest pulse (optical or electrical).

What is claimed is:

1. A photomultiplier tube comprising a housing having therein:
   a. a photocathode for receiving light and producing emission of electrons in proportion to the intensity of the light,
   b. accellerating means for accellerating electrons received from the photocathode,
   c. means connected to the photocathode for receiving a voltage signal, the voltage signal passing through the photocathode and negatively biasing the photocathode relative to the accellerating means so as to cause electrons emitted by the photocathode to be accellerated to the accellerating means,
   d. electron multiplication means for performing electron multiplication on electrons received from the accellerating means,
   e. anode means for producing an analog electrical signal output of electrons received from the electron multiplication means, and
   f. means coupling the accellerating means, the electrons multiplication means and the anode means to a high voltage source for negatively biasing the accellerating means relative to the electron multiplication means and for negatively biasing the electron multiplication means relative to the anode means so as to cause electrons at the accellerating means to be moved to the electron multiplication means and then from the electron multiplication means to the anode means.

2. A photomultiplier tube comprising a housing having therein:
   a. a photocathode for receiving light and producing emission of electrons in proportion to the intensity of the light, the photocathode being in a transmission line configuration and having an input side and an output side,
   b. accellerating means for accellerating electrons emitted by the photocathode,
   c. electron multiplication means for performing electron multiplication on the electrons emitted from the accellerating means,
   d. anode means for receiving electrons from the electron multiplication means and producing an analog electrical signal output,
   e. means for causing electrons emitted by the photocathode to move through the accellerating means and the electron multiplication means and then impinge on the anode means,
   f. means connected to the photocathode for receiving and transmitting out an ultrafast voltage signal, and
   g. a variable aperture on the input side of the photocathode.

3. The photomultiplier tube of claim 2 and wherein the photocathode is a microstrip line.

4. The photomultiplier tube of claim 2 and wherein the photocathode is slot line.

5. The photomultiplier tube of claim 2 and wherein the photocathode is a coplanar waveguide.

6. The photomultiplier tube of claim 2 and wherein the photocathode is a coplanar strip.

7. The photomultiplier tube of claim 2 and wherein said means connected to said photocathode comprises high speed stripline launchers having 18 GHZ or 40 GHZ bandwidth.

8. The photomultiplier tube of claim 2 and wherein the variable aperture size is from about 5.0 um to 2 mm.

9. The photomultiplier tube of claim 2 and wherein the photocathode includes a photoconductive material selected from the group consisting of AG—O—Cs, Sb—Cs, Bialkali (Sb—rb—Cs$_1$), multialkali (S-20) and Ga—As—O—Cs.

10. A system for time resolving a voltage pulse from a test device comprising:
 a. means for generating a pulse of light,
 b. means for splitting the pulse of light into first and second beam paths,
 c. a photomultiplier tube disposed along the first beam path, said photomultiplier tube having a photocathode having a transmission line configuration, the pulse of light travelling along the first beam path striking the photocathode,
 d. a voltage pulse generator for receiving the light from the second beam path and outputting a voltage pulse in response thereto, said test device being coupled to said output, and
 e. means connecting the output of the test device to the photocathode of the photomultiplier tube so as to apply a bias voltage to said photocathode.

11. A system for time resolving luminescence from a sample comprising:
 a. means for generating a pulse of light,
 b. means for splitting the pulse of light into first and second beam paths, said sample being disposed along said second beam path,
 c. a photomultiplier tube for receiving the light emitted by the sample on illumination by the portion of the light pulse travelling along the second beam path, said photomultiplier tube having a photocathode having a transmission line configuration,
 d. a voltage pulse generator for receiving the light pulse traveling along the first beam path and outputting a voltage pulse in response thereto, and
 e. means connecting the output of the voltage pulse generator to the photocathode of the photomultiplier tube so as to apply a bias voltage pulse to said photocathode.

12. The system of either claim 10 or claim 11 and further including recording means.

13. The photomultiplier tube of claim 2 and wherein said photocathode comprises a substrate of dielectric material, a layer of photoconductive material on top of said substrate and a layer of conductive material below said substrate.

14. The photomultiplier tube of claim 13 and wherein said dielectric is glass and said conductive material is gold or copper.

15. The photomultiplier tube of claim 2 and wherein the aperture varies in diameter from 20 μm to 200 μm.

16. The photomultiplier tube of claim 2 and wherein the accellerating means is a mesh.

17. The photomultiplier tube of claim 2 and wherein the electron multiplication means is a dynode chain.

18. The photomultiplier tube of claim 2 and wherein the means for moving electrons is a high voltage.

* * * * *